(12) United States Patent
Schraven et al.

(10) Patent No.: US 8,809,576 B2
(45) Date of Patent: Aug. 19, 2014

(54) METHOD FOR PRODUCING A FREE ACID FROM THE SALT THEREOF

(75) Inventors: Alexander Schraven, Issum (DE); Thomas Tacke, Alzenau (DE); Thomas Haas, Muenster (DE); Christoph Kobler, Alzenau (DE); Dieter Buss, Aschaffenburg (DE); Axel Ronneburg, Erlensee (DE); Olivier Zehnacker, Recklinghausen (DE)

(73) Assignee: Evonik Degussa GmbH, Essen (DE)

( * ) Notice: Subject to any disclaimer, the term of this patent is extended or adjusted under 35 U.S.C. 154(b) by 506 days.

(21) Appl. No.: 13/141,456

(22) PCT Filed: Feb. 1, 2010

(86) PCT No.: PCT/EP2010/051170
§ 371 (c)(1),
(2), (4) Date: Jun. 22, 2011

(87) PCT Pub. No.: WO2010/094554
PCT Pub. Date: Aug. 26, 2010

(65) Prior Publication Data
US 2011/0257429 A1   Oct. 20, 2011

(30) Foreign Application Priority Data
Feb. 19, 2009   (DE) .................. 10 2009 009 580

(51) Int. Cl.
*C07F 9/22* (2006.01)

(52) U.S. Cl.
USPC ............................................. 562/8

(58) Field of Classification Search
None
See application file for complete search history.

(56) References Cited

U.S. PATENT DOCUMENTS

| | | | |
|---|---|---|---|
| 5,817,870 | A | 10/1998 | Haas et al. |
| 5,831,121 | A | 11/1998 | Haas et al. |
| 6,291,708 | B1 | 9/2001 | Cockrem |
| 7,393,972 | B2 | 7/2008 | Pascaly et al. |
| 8,372,595 | B2 | 2/2013 | Schaffer et al. |
| 8,604,227 | B2 | 12/2013 | Petrat et al. |
| 2004/0210087 | A1 | 10/2004 | Meng et al. |
| 2010/0068773 | A1 | 3/2010 | Marx et al. |
| 2010/0190224 | A1 | 7/2010 | Poetter et al. |
| 2010/0210871 | A1 | 8/2010 | Kobler et al. |
| 2010/0261237 | A1 | 10/2010 | Verseck et al. |
| 2010/0291644 | A1 | 11/2010 | Marx et al. |
| 2010/0324257 | A1 | 12/2010 | Karau et al. |
| 2011/0039313 | A1 | 2/2011 | Verseck et al. |
| 2011/0118433 | A1 | 5/2011 | Pötter et al. |
| 2011/0118504 | A1 | 5/2011 | Haas et al. |
| 2012/0034665 | A1 | 2/2012 | Haas et al. |
| 2012/0041216 | A1 | 2/2012 | Sieber et al. |
| 2012/0245375 | A1 | 9/2012 | Hannen et al. |
| 2012/0264182 | A1 | 10/2012 | Reinecke et al. |
| 2013/0035403 | A1 | 2/2013 | Schaffer et al. |
| 2013/0052700 | A1 | 2/2013 | Poetter et al. |
| 2013/0092233 | A1 | 4/2013 | Pawlik et al. |
| 2013/0130319 | A1 | 5/2013 | Schaffer et al. |
| 2013/0165672 | A1 | 6/2013 | Klasovsky et al. |
| 2013/0165685 | A1 | 6/2013 | Hannen et al. |
| 2013/0183725 | A1 | 7/2013 | Poetter et al. |
| 2013/0245276 | A1 | 9/2013 | Klasovsky et al. |
| 2013/0331580 | A1 | 12/2013 | Klasovksy et al. |

FOREIGN PATENT DOCUMENTS

| | | |
|---|---|---|
| DE | 10 2006 052 311 | 5/2008 |
| WO | 00 64850 | 11/2000 |
| WO | 02 90312 | 11/2002 |
| WO | 2006 069129 | 6/2006 |
| WO | 2006 124633 | 11/2006 |
| WO | WO 2006124633 A1 * | 11/2006 |
| WO | WO 2008042958 A2 * | 4/2008 |
| WO | 2009 156214 | 12/2009 |
| WO | 2010 000506 | 1/2010 |
| WO | 2010 006834 | 1/2010 |
| WO | 2010 094630 | 8/2010 |

OTHER PUBLICATIONS

McMaster et al., The Neutral Ammonium Salts of Organic Acids and their substituted Derivatives, J. Amer. Chem. Soc., 1918, 40(4), 683-693.*
International Search Report issued Apr. 12, 2010 in PCT/EP10/51170 filed Feb. 1, 2010.
U.S. Appl. No. 13/001,204, filed Dec. 23, 2010, Reinecke, et al.
U.S. Appl. No. 13/002,519, filed Jan. 4, 2011, Haas, et al.
U.S. Appl. No. 61/239,634, filed Sep. 9, 2009, Kobler, et al.
U.S. Appl. No. 14/126,607, filed Dec. 16, 2013, Hass, et al.
U.S. Appl. No. 14/233,505, filed Jan. 17, 2014, Poetter, et al.
U.S. Appl. No. 14/237,121, filed Feb. 4, 2014, Haas, et al.
U.S. Appl. No. 14/238,576, filed Feb. 12, 2014, Schaffer, et al.
U.S. Appl. No. 14/238,591, filed Feb. 12, 2014, Schaffer, et al.

* cited by examiner

*Primary Examiner* — Porfirio Nazario Gonzalez
*Assistant Examiner* — Kofi Adzamli
(74) *Attorney, Agent, or Firm* — Oblon, Spivak, McClelland, Maier & Neustadt, L.L.P.

(57) ABSTRACT

The invention relates to an improved method for releasing an organic acid, preferably a carbon, sulfone or phosphone acid, particularly an alpha or beta hydroxycarbon acid, from the ammonia salt thereof by releasing and removing ammoniac and simultaneous extraction of the released acid, having an amine as a suitable extraction means from the aqueous phase. This method corresponds to a reactive extraction. The reactive extraction of an organic acid from the aqueous ammonia salt solution thereof can be significantly improved by the use of a strip medium or carrier gas, such as nitrogen, air, water vapor or inert gases such as argon. The released ammoniac is removed from the aqueous solution by the continuous gas flow and can be resupplied into a production process. The free acid can be obtained by a method such as distillation, rectification, crystallization, reextraction, chromatography, adsorption or by a membrane method from the extraction means.

12 Claims, 3 Drawing Sheets

METHOD FOR PRODUCING A FREE ACID FROM THE SALT THEREOF

This application is a National Stage of PCT/EP10/051170 filed Feb. 1, 2010 and claims the benefit of DE 10 2009 009 580/2 filed Feb. 19, 2009.

INTRODUCTION

The present invention relates to a novel, improved process for preparing and isolating free organic acids such as carboxylic acids, sulphonic acids, phosphonic acids and especially hydroxycarboxylic acids from the corresponding ammonium salts thereof.

Organic acids include the group of the substituted carboxylic acids (I), sulphonic acids (II) and phosphonic acids (III):

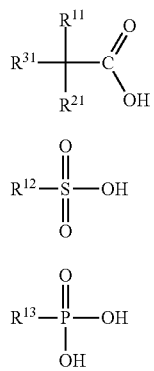

Hydroxycarboxylic acids are specific carboxylic acids which possess both a carboxyl group and a hydroxyl group. Most naturally occurring representatives are alpha-hydroxycarboxylic acids, i.e. the hydroxyl group is on a carbon atom adjacent to the carboxyl group.

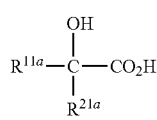

Important alpha-hydroxycarboxylic acids are, as well as lactic acid, glycolic acid, citric acid and tartaric acid, also 2-hydroxyisobutyric acid as a precursor of methacrylic acid and methacrylic esters. These find their main field of use in the preparation of polymers and copolymers with other polymerizable compounds.

A further class of hydroxycarboxylic acids is that of the beta-hydroxycarboxylic acids.

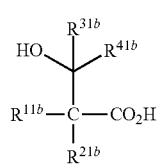

Important beta-hydroxycarboxylic acids are, for example, 3-hydroxypropionic acid, 3-hydroxybutyric acid, 3-hydroxyvaleric acid, 3-hydroxyhexanoic acid, 3-hydroxyheptanoic acid, 3-hydroxyoctanoic acid and 3-hydroxyisobutyric acid. One example which has been described as naturally occurring is 3-hydroxyisobutyric acid, in *Valine metabolism. Gluconeogenesis from 3-hydroxyisobutyrate*, Letto J et al., Biochem J. 1986 Dec. 15; 240(3):909-12. 3-Hydroxyisobutyric acid, just like 2-hydroxyisobutyric acid, can likewise serve as a precursor for methacrylic acid and methacrylic esters.

All organic acids form, with ammonia, the corresponding ammonium salts IV, V and VI.

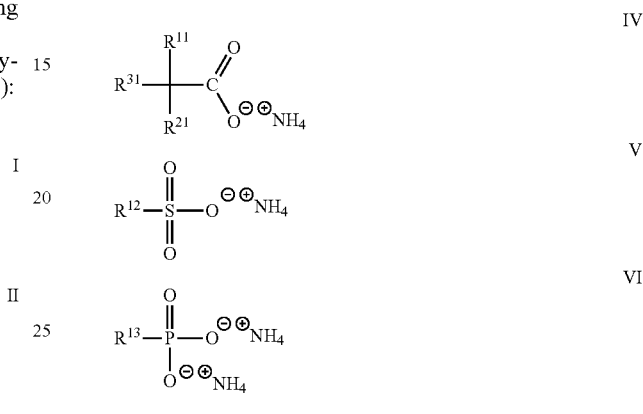

STATE OF THE ART

According to the state of the art, hydroxycarboxylic acids are preferably prepared from their parent cyanohydrins with the aid of mineral acids, for example hydrochloric acid, phosphoric acid or preferably with sulphuric acid. To isolate the free acid, only the mineral acid used for hydrolysis is neutralized subsequently with a base, preferably ammonia. All of the mineral acid and the base used for neutralization are necessarily obtained in these processes in at least stoichiometric and hence very large amounts in the form of mineral salts, usually in the form of ammonium sulphate. These salts can be disposed of on the market only with difficulty and only with losses compared to the feedstocks. Owing to this problem, large amounts of these salts even have to be disposed of with disposal costs. Another chemical process is the hydrolysis of cyanohydrin with inorganic bases, for example sodium hydroxide. It is likewise necessary here to release the alpha-hydroxycarboxylic acid by adding a mineral acid in stoichiometric amounts. The hydrolysis of cyanohydrins likewise goes to the stage of the ammonium salt with titanium dioxide as the catalyst. The salt problem remains the same.

alpha- and beta-hydroxycarboxylic acids can also be prepared fermentatively with the aid of microorganisms or enzymatically. This affords the hydroxycarboxylic acid in the form of the ammonium salt. It is released by adding the stoichiometric amount of a mineral acid. This likewise gives rise to stoichiometric amounts of ammonium salts.

Processes in which no salt burden occurs are currently uneconomic for the industrial scale for reasons of cost. One example thereof is the esterification of an ammonium salt of an alpha-hydroxycarboxylic acid with an alcohol and subsequent hydrolysis of the ester with an acid catalyst (JP7194387).

In order to prepare free carboxylic acids from the ammonium salts, there are various processes based on the thermal decomposition of the ammonium carboxylates (Scheme 1):

Scheme 1

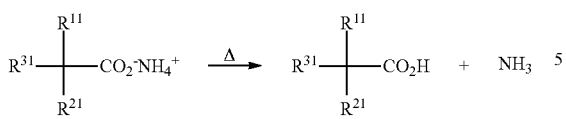

According to GB967352, a small amount of water is added to an ammonium salt of an unsaturated fatty acid, and the mixture is heated at total reflux (80° C.) or higher in organic solvents in order to free or to remove ammonia to obtain the unsaturated fatty acid.

According to JP54115317, an organic solvent which forms an azeotropic mixture with water is added to a 10-50% aqueous solution of ammonium methacrylate, and the solution which arises is heated to 60-100° C. As a result, water is distilled off as an azeotropic mixture and ammonia is removed simultaneously in order to obtain free methacrylic acid.

According to JP7330696, a 10-80% aqueous solution of an ammonium salt of an acidic amino acid is heated with addition of water. Ammonia and water are distilled off and the amino acid is released.

In these processes, ammonia is in principle removed easily when the carboxylic acid has a high dissociation constant. Their disadvantages are, however, that the degree of dissociation of ammonium ions from ammonium salts of carboxylic acids is low for strong acids with $pK_a$ values less than 4, such as alpha-hydroxycarboxylic acids. It is therefore very difficult to remove ammonia from the salts of strong acids. In order to remove the majority of ammonia, a long period is required, or it is necessary to add a large amount of water or of organic solvents. In the abovementioned processes, 50% or more of the corresponding carboxylic acid remains as the ammonium salt.

U.S. Pat. No. 6,066,763 describes a process for preparing alpha-hydroxycarboxylic acids, which proceeds without the inevitable occurrence of large amounts of salts which can be disposed of only with difficulty, if at all. In this process, the starting materials used are the ammonium salts of the corresponding alpha-hydroxycarboxylic acids, said salts being obtainable from the corresponding cyanohydrins with the aid of enzymes (nitrilases). The salt is heated in the presence of water and a solvent. Preferred solvents have a boiling point of >40° C. and form an azeotrope with water. The distillative removal of the azeotropic mixture releases ammonia, which escapes in gaseous form via the condenser. The corresponding alpha-hydroxycarboxylic acid accumulates in the bottom of the distillation apparatus. However, the removal of the water at elevated temperature results in large amounts of the initially released alpha-hydroxycarboxylic acid being converted by intra- or else intermolecular esterification to dimers and polymers of the alpha-hydroxycarboxylic acid in question. These subsequently have to be converted back to the monomeric alpha-hydroxycarboxylic acid in question by heating with water under elevated pressure. Another disadvantage is the long residence times in both process stages. They are 4 hours in the examples mentioned. Since the solvent is kept at boiling for the whole time in stage 1, the steam consumption is uneconomically high. The cause of this is the release of the alpha-hydroxycarboxylic acid, which becomes more difficult with increasing depletion of ammonia. It does not succeed 100%. After the end of the reaction, 3-4% bound ammonia still remains in the bottoms. Under the reaction conditions, another by-product which occurs is the corresponding amide of the alpha-hydroxycarboxylic acid, which is only partly converted to the corresponding ammonium salt by hydrolysis in stage 2 of the process (Scheme 2).

Scheme 2

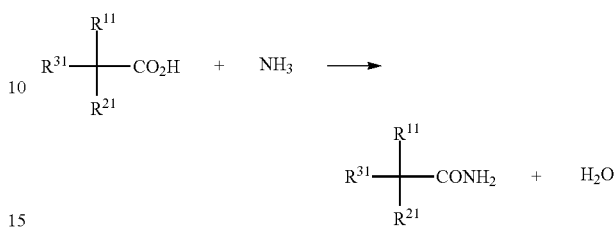

The alpha-hydroxycarboxylic acids obtained possess only a purity of approx. 80%, and so a further purification by means of liquid-liquid extraction or crystallization is advisable.

In patent publication WO 00/59847, the ammonium salt solutions of the alpha-hydroxycarboxylic acids are brought to a concentration of >60% under reduced pressure. The conversion to dimers or polymers of the corresponding alpha-hydroxycarboxylic acids is intended to be less than 20%. Passing an inert gas through, preferably steam, releases and drives out ammonia. Using the example of 2-hydroxy-4-methylthiobutyric acid, 70% free acid is achieved; the remainder consists of the unconverted ammonium salt of 2-hydroxy-4-methylthiobutyric acid and the corresponding dimers.

US 2003/0029711 A1 describes a process for obtaining organic acids, including from aqueous solutions of the ammonium salts, with addition of a hydrocarbon as an entraining agent. Heating the mixture affords a gaseous product stream which comprises an azeotrope consisting of the organic acid and the entraining agent. In order to isolate the acid from this product stream, further steps such as condensation and additional distillations must be carried out. Furthermore, this process also requires the addition of additional chemicals (entraining agents), which makes the process significantly more costly, specifically for use on the industrial scale.

U.S. Pat. No. 6,291,708 B1 describes a process in which an aqueous solution of an ammonium salt is mixed with a suitable alcohol, and this alcohol-water mixture is then heated under elevated pressure in order to decompose the ammonium salt thermally to the free acid and ammonia. At the same time, a suitable gas as an entraining agent is contacted with the alcohol-water mixture, so as to drive out a gaseous product stream comprising ammonia, water and a portion of the alcohol, while at least 10% of the alcohol remains in the liquid phase and reacts with the free acid to give the corresponding ester. The disadvantages of this process include the necessity of additional chemicals (alcohol and a gas as an entraining agent) and the partial conversion of the free carboxylic acid formed to the ester, which in turn has to be hydrolysed in order to obtain the free carboxylic acid.

In DE 10 2006 052 311 A1 (published specification), the ammonium salt of an alpha-hydroxycarboxylic acid is heated in the presence of a tertiary amine with release of the ammonia and formation of the salt of tertiary amine and alpha-hydroxycarboxylic acid in question. Subsequently, the salt is dissociated thermally and the tertiary amine formed is recovered by distillation. The free alpha-hydroxycarboxylic acid remains in the distillation bottoms. The purity of the alpha-hydroxycarboxylic acids obtained is 95%.

In DE 10 2006 049 767 A1 (published specification), this process is applied to the preparation of 2-hydroxy-4-methylthiobutyric acid from the corresponding 2-hydroxy-4-methylthiobutyramide. With N-methylmorpholine, 2-hydroxy-4-methylthiobutyric acid is formed at 180° C. and 6 bar in a purity of 95% with 96% yield. The use of other tertiary amines gives similar results.

In DE 10 2006 049 768 A1 (published specification), the 2-hydroxy-4-methylthiobutyramide formed by mineral acid hydrolysis of 2-hydroxy-4-methylthiobutyronitrile is extracted with a polar water-immiscible solvent. Preferred solvents are ethers, ketones and trialkylphosphine oxides, also in mixtures with various hydrocarbons. The solvent is removed by distillation and the resulting 2-hydroxy-4-methylthiobutyramide is base-hydrolysed. The bases used are tertiary amines, which can be removed again by distillation from the salts formed with release of the 2-hydroxy-4-methylthiobutyric acid. The temperatures in this process are between 130 and 180° C. at 6 bar.

The disadvantages of the latter processes are the high temperatures of 130 to 180° C. employed, which are not very economic, and the pressure range of 6 bar requires increased capital costs in the industrial implementation.

In U.S. Pat. No. 6,815,560 and the patent publications cited there, the free 2-hydroxy-4-methylthiobutyric acid prepared by sulphuric acid hydrolysis is extracted from the hydrolysis solution with a water-immiscible solvent, preferably isobutyl methyl ketone. The extractant is recovered by distillation; the 2-hydroxy-4-methylthiobutyric acid remains in the distillation bottoms in its monomeric and dimeric forms. The addition of water adjusts the thermodynamic equilibrium between the two forms.

WO9815517 describes a process for extracting lactic acid with a basic organic solvent or water-immiscible amines.

DE 102006052311 describes a process for preparing free α-hydroxycarboxylic acids by heating the corresponding ammonium carboxylates in the presence of tertiary amines with distillative removal of the ammonia which forms, followed by further distillative removal and accompanying formation of the tertiary amine and of the free α-hydroxycarboxylic acid.

U.S. Pat. No. 4,275,234 describes an extractive process for carboxylic acids with amines as the extractant, comprising an additional, aqueous re-extraction step which leaves the carboxylic acid present again in aqueous solution.

U.S. Pat. No. 4,444,881 describes a process for isolating organic acids from fermentation broth by converting the acid to the calcium salt thereof, addition of a water-soluble tertiary amine carbonate to form the trialkylammonium salt and precipitating calcium carbonate, concentrating the trialkylammonium salt solution and dissociating the trialkylammonium salt by heating.

EP 1385593 describes a process for working up short-chain carboxylic acids from a solution of the alkylammonium complexes thereof by distillation with addition of an azeotroping hydrocarbon under conditions under which the alkylammonium complex decomposes to the free short-chain carboxylic acid and the alkylamine.

U.S. Pat. No. 5,510,526 describes a process for working up free lactic acid from a fermentation broth by extraction with an extractant comprising a water-immiscible trialkylamine with at least 18 carbon atoms in the presence of $CO_2$, removing the organic phase from the aqueous phase and finally separating the free lactic acid from the organic phase.

WO02090312 describes a process for purifying free carboxylic acids from aqueous solutions, in which the aqueous solution is heated as a mixture with an organic solvent and the free acid is thus obtained.

U.S. Pat. No. 5,132,456 describes a multistage process for purifying free carboxylic acids from an aqueous medium, in which the carboxylic acid is first extracted with an acid-absorbing medium and, after separating this medium from the aqueous medium/from this acid-absorbing medium, the carboxylic acid is re-extracted again as the ammonium carboxylate with water-soluble amines. Subsequently, the ammonium carboxylate is dissociated.

A disadvantage of all processes is that large amounts of aqueous streams are obtained or products which cannot be fed back to the process arise and thus remain as waste.

OBJECT OF THE INVENTION

Against the background of the disadvantages of the prior art, it was an object of the present invention to find an inexpensive and environmentally compatible process for isolating free organic acids such as carboxylic acids, sulphonic acids, phosphonic acids and especially alpha- and beta-hydroxycarboxylic acids from the ammonium salts thereof, which does not form a salt burden as a coproduct and is completely back-integrated by means of closed circuits.

The technical object is achieved by a process for converting ammonium salts of organic acids to the particular free organic acid, wherein an aqueous solution of the ammonium salt is contacted with at least one organic extractant selected from the group comprising amines of the general formula (0)

formula (0)

where $R^1$, $R^2$ and $R^3$ are independently identical or nonidentical, branched or unbranched, optionally substituted hydrocarbon radicals or H, and the salt is dissociated at temperatures and pressures at which the aqueous solution and the extractant are in the liquid state, and a stripping medium or entraining gas is introduced in order to remove $NH_3$ from the aqueous solution, and at least a portion of the free organic acid formed is transferred to the organic extractant.

The term "amine" in the context of the present invention explicitly excludes ammonia, i.e. $R^1$, $R^2$ and $R^3$=H in formula (O). Preference is given to using amines in which $R^1$, $R^2$ and $R^3$ are independently identical or nonidentical, branched or unbranched, unsubstituted alkyl radicals having preferably 1 to 20, more preferably 1 to 18, most preferably 1 to 16, carbon atoms, or H. The amines used are preferably alkylamines having at least 16 carbon atoms, preferably trialkylamines and more preferably trialkylamines selected from the group comprising trihexylamines, trioctylamine, tridecylamine, tridodecylamines. In particular embodiments of the process according to the invention, it may be advantageous to use amines with a relatively high base strength; in this case, it is preferred that the amines used are dialkylamines and preferably dialkylamines selected from the group comprising diisotridecylamine, bis(2-ethylhexyl)amine, lauryltrialkylmethylamines, diundecylamine, didecylamine.

The invention thus provides a process wherein the ammonium salt of organic acids is converted by means of reactive extraction using a stripping medium or entraining gas, for example by driving out (stripping) with steam, to the free organic acid which is transferred into the organic extractant. It is preferred that at least 50%, preferably at least 80%, more preferably at least 90% and most preferably at least 95% of the free organic acid formed is transferred into the organic extractant.

In a preferred process, the conversion is effected at pressures of 0.01 bar to 10 bar, particularly of 0.05 bar to 8 bar, preferably of 0.1 bar to 6 bar.

Moreover, it is preferred that the salt dissociation is performed at temperatures of 20° C. to 300° C., more preferably of 40° C. to 200° C., further preferably of 50° C. to 160° C.

The temperature has a high influence on the rate of formation of the free acid and the end yield thereof. The temperature is guided by the extractant used and is, according to the invention, below the boiling point of the aqueous solution or of a possible azeotrope, the boiling point of the aqueous solution or of any azeotrope which forms depending of course on the particular pressure applied.

As already described above, the salt dissociation in the process according to the invention is performed at temperatures and pressures at which the aqueous solution and the extractant are in liquid form and not in solid form and not in gaseous form, i.e. below the boiling temperature, which depends on the particular pressure applied, of the aqueous solution or of any azeotropic mixture which forms.

According to the invention, the starting concentration of the ammonium salt of the organic acid in the aqueous solution used is preferably in the range up to 60% by weight, preferably up to 40% by weight, further preferably up to 20% by weight, further preferably up to 18% by weight, more preferably up to 15% by weight, especially preferably up to 12% by weight and most preferably up to 10% by weight, based on the overall aqueous solution. In the course of the salt dissociation reaction, the corresponding concentration of the salt decreases.

Moreover, it is preferred that the extractant used is a sparingly water-miscible or entirely water-immiscible amine. The weight ratio of aqueous solution and organic extractant is preferably from 1:100 to 100:1, preferably from 1:10 to 10:1, more preferably from 1:5 to 5:1.

According to the present invention, the organic acid may be selected from the group of monocarboxylic acid, dicarboxylic acid, tricarboxylic acid, ascorbic acid, sulphonic acid, phosphonic acid, hydroxycarboxylic acid, especially alpha-hydroxycarboxylic acid and beta-hydroxycarboxylic acid.

In further process steps, according to the invention, after the salt dissociation has ended, the organic acid formed can be obtained from the organic extractant.

In a preferred embodiment, the organic acid corresponds to a carboxylic acid of the general formula X—CO$_2$H where X is an organic radical selected from the group comprising unsubstituted and mono- or polysubstituted, branched and straight-chain alkyl radicals, cycloalkyl radicals, alkenyl radicals having one or more double bonds, alkynyl radicals having one or more triple bonds, aryl radicals, alkylaryl radicals, arylalkyl radicals, arylalkenyl radicals, alkyloxyalkyl radicals, hydroxyalkyl radicals and alkylthioalkyl radicals.

In one alternative, it is preferred that X is an organic radical selected from the group of ($C_1$-$C_{18}$)-alkyl radicals, ($C_3$-$C_{18}$)-cycloalkyl radicals, ($C_2$-$C_{26}$)-alkenyl radicals having one or more double bonds, ($C_2$-$C_{26}$)-alkynyl radicals having one or more triple bonds, ($C_6$-$C_{10}$)-aryl radicals, especially phenyl radicals, ($C_1$-$C_{18}$)-alkyl-($C_6$-$C_{10}$)-aryl radicals, ($C_6$-$C_{10}$)-aryl-($C_1$-$C_{18}$)-alkyl radicals, ($C_6$-$C_{10}$)-aryl-($C_2$-$C_{18}$)-alkenyl radicals, ($C_1$-$C_{18}$)-alkyloxy-($C_1$-$C_{18}$)-alkyl radicals, ($C_1$-$C_{18}$)-hydroxyalkyl radicals and ($C_1$-$C_{18}$)-alkylthio-($C_1$-$C_{18}$)-alkyl radicals.

In another alternative, X is preferably $CR^{10}R^{20}R^{30}$ where $R^{10}$=H, OH, $OR^{40}$, $NH_2$, $NHR^{40}$, $NR^{40}R^{50}$, Cl, Br, I, F, where $R^{20}$, $R^{30}$, $R^{40}$ and $R^{50}$ are each independently selected from the group comprising H, unsubstituted and mono- or polysubstituted, branched and straight-chain ($C_1$-$C_{18}$)-alkyl radicals, ($C_3$-$C_{18}$)-cycloalkyl radicals, ($C_2$-$C_{26}$)-alkenyl radicals having one or more double bonds, ($C_6$-$C_{10}$)-aryl radicals, especially phenyl radicals, ($C_1$-$C_{18}$)-alkyl-($C_6$-$C_{10}$)-aryl radicals, ($C_6$-$C_{10}$)-aryl-($C_1$-$C_{18}$)-alkyl radicals, especially benzyl radicals, ($C_1$-$C_{18}$)-alkyloxy-($C_1$-$C_{18}$)-alkyl radicals, ($C_1$-$C_{18}$)-hydroxyalkyl radicals and ($C_1$-$C_{18}$)-alkylthio-($C_1$-$C_{18}$)-alkyl radicals.

The organic acid is preferably selected from the group of acetic acid, propionic acid, butyric acid, valeric acid, caproic acid, oenanthic acid, caprylic acid, pelargonic acid, capric acid, lauric acid, palmitic acid, stearic acid, omega-3 fatty acids such as linolenic acid, omega-6 fatty acids such as linoleic acid and arachidonic acid, omega-9 fatty acids such as oleic acid and nervonic acid, salicylic acid, benzoic acid, ferulic acid, cinnamic acid, vanillic acid, gallic acid, hydroxycinnamic acids, hydroxybenzoic acids, 3-hydroxypropionic acid, 3-hydroxyisobutyric acid and 2-hydroxyisobutyric acid.

In an alternative process the organic acid corresponds to a dicarboxylic acid of the general formula $H_2OC$—Y—$CO_2H$ where Y is an organic radical selected from the group comprising unsubstituted and mono- or polysubstituted, branched and straight-chain alkanediyl radicals, cycloalkanediyl radicals, alkenediyl radicals having one or more double bonds, alkynediyl radicals having one or more triple bonds, aryldiyl radicals, alkylaryldiyl radicals, arylalkanediyl radicals, arylalkenediyl radicals, alkyloxyalkanediyl radicals, hydroxyalkanediyl radicals and alkylthioalkanediyl radicals.

The suffix "-diyl" indicates in this context that both carboxylic acid groups of the dicarboxylic acid are bonded to this radical. The carboxylic acid groups may each independently be bonded to any carbon atoms of the organic radical, for example geminally, vicinally or to nonadjacent carbon atoms, and the carbon atoms to which the carboxylic acid groups are bonded may either be in terminal positions or within the radical.

It is preferred that Y is defined as follows: an organic radical selected from the group of unsubstituted and mono- or polysubstituted, branched and straight-chain ($C_1$-$C_{18}$)-alkanediyl radicals, ($C_3$-$C_{18}$)-cycloalkanediyl radicals, ($C_2$-$C_{26}$)-alkenediyl radicals having one or more double bonds, ($C_2$-$C_{20}$)-alkynediyl radicals having one or more triple bonds, ($C_6$-$C_{10}$)-aryldiyl radicals, especially phenyldiyl radicals, ($C_1$-$C_{18}$)-alkyl-($C_6$-$C_{10}$)-aryldiyl radicals, ($C_6$-$C_{10}$)-aryl-($C_1$-$C_{18}$)-alkanediyl radicals, ($C_6$-$C_{10}$)-aryl-($C_1$-$C_{18}$)-alkenediyl radicals, ($C_1$-$C_{18}$)-alkyloxy-($C_1$-$C_{18}$)-alkanediyl radicals, ($C_1$-$C_6$)-hydroxyalkanediyl radicals and ($C_1$-$C_{18}$)-alkylthio-($C_1$-$C_{18}$)-alkanediyl radicals, any substituents being selected from the group comprising OH, $OR^{10'}$, $NH_2$, $NHR^{10'}$, $NR^{10'}R^{20'}$, Cl, Br, I and F, where $R^{10'}$, $R^{20'}$ are each independently selected from the group comprising H, unsubstituted and mono- or polysubstituted, branched and straight-chain ($C_1$-$C_{18}$)-alkyl radicals, ($C_3$-$C_{18}$)-cycloalkyl radicals, ($C_2$-$C_{26}$)-alkenyl radicals having one or more double bonds, ($C_6$-$C_{10}$)-aryl radicals, especially phenyl radicals, ($C_1$-$C_{18}$)-alkyl-($C_6$-$C_{10}$)-aryl radicals, ($C_6$-$C_{10}$)-aryl-($C_1$-$C_{18}$)-alkyl radicals, especially benzyl radicals, ($C_1$-$C_{18}$)-alkyloxy-($C_1$-$C_{18}$)-alkyl radicals, ($C_1$-$C_{18}$)-hydroxyalkyl radicals and ($C_1$-$C_{18}$)-alkylthio-($C_1$-$C_{18}$)-alkyl radicals.

The organic acid is preferably selected from the group of succinic acid, oxalic acid, malonic acid, glutaric acid, adipic acid, pimelic acid, suberic acid, azelaic acid, sebacic acid, fumaric acid, itaconic acid, methylmalonic acid, phthalic acid, terephthalic acid, isophthalic acid.

In a further alternative process the organic acid is a tricarboxylic acid of the general formula Ic:

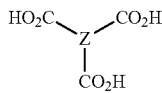

Ic where Z is an organic radical selected from the group comprising unsubstituted and mono- or polysubstituted, branched and straight-chain alkanetriyl radicals, cycloalkanetriyl radicals, alkenetriyl radicals having one or more double bonds, alkynetriyl radicals having one or more triple bonds, aryltriyl radicals, alkylaryltriyl radicals, arylalkanetriyl radicals, arylalkenetriyl radicals, alkyloxyalkanetriyl radicals, hydroxyalkanetriyl radicals and alkylthioalkanetriyl radicals. The suffix "-triyl" indicates here that the three carboxylic acid groups of the tricarboxylic acid are bonded to this radical. The carboxylic acid groups may each independently be bonded to any carbon atoms of the organic radical, for example geminally, vicinally or to nonadjacent carbon atoms, where the carbon atoms to which the carboxylic acid groups are bonded may either be in terminal positions or within the radical.

Moreover, it is preferred that Z is defined as follows: unsubstituted and mono- or polysubstituted, branched and straight-chain $(C_1-C_{18})$-alkanetriyl radicals, $(C_3-C_{18})$-cycloalkanetriyl radicals, $(C_2-C_{26})$-alkenetriyl radicals having one or more double bonds, $(C_2-C_{26})$-alkynetriyl radicals having one or more triple bonds, $(C_6-C_{10})$-aryltriyl radicals, especially phenyltriyl radicals, $(C_1-C_{18})$-alkyl-$(C_6-C_{10})$-aryltriyl radicals, $(C_6-C_{10})$-aryl-$(C_1-C_{18})$-alkanetriyl radicals, $(C_6-C_{10})$-aryl-$(C_1-C_{18})$-alkenetriyl radicals, $(C_1-C_{18})$-alkyloxy-$(C_1-C_{18})$-alkanetriyl radicals, $(C_1-C_6)$-hydroxyalkanetriyl radicals and $(C_1-C_{18})$-alkylthio-$(C_1-C_{18})$-alkanetriyl radicals, any substituents being selected from the group comprising OH, $OR^{10'''}$, $NH_2$, $NHR^{10'''}$, $NR^{10'''}R^{20'''}$, Cl, Br, I and F, where $R^{10'''}$, $R^{20'''}$ are each independently selected from the group comprising H, unsubstituted and mono- or polysubstituted, branched and straight-chain $(C_1-C_{18})$-alkyl radicals, $(C_3-C_{18})$-cycloalkyl radicals, $(C_2-C_{26})$-alkenyl radicals having one or more double bonds, $(C_6-C_{10})$-aryl radicals, especially phenyl radicals, $(C_1-C_{18})$-alkyl-$(C_6-C_{10})$-aryl radicals, $(C_6-C_{10})$-aryl-$(C_1-C_{18})$-alkyl radicals, especially benzyl radicals, $(C_1-C_{18})$-alkyloxy-$(C_1-C_{18})$-alkyl radicals, $(C_1-C_{18})$-hydroxyalkyl radicals and $(C_1-C_{18})$-alkylthio-$(C_1-C_{18})$-alkyl radicals.

In a preferred embodiment, the organic acid is selected from the group of citric acid, cyclopentane-1,2,3-tricarboxylic acid, cyclopentane-1,2,4-tricarboxylic acid, 2-methylcyclopentane-1,2,3-tricarboxylic acid, 3-methylcyclopentane-1,2,4-tricarboxylic acid.

In a further process, the organic acid corresponds to a sulphonic acid of the general formula II:

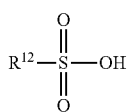

II where $R^{12}$ is an organic radical selected from the group comprising unsubstituted and mono- or polysubstituted, branched and straight-chain alkyl radicals, cycloalkyl radicals, alkenyl radicals having one or more double bonds, alkynyl radicals having one or more triple bonds, aryl radicals, alkylaryl radicals, arylalkyl radicals, arylalkenyl radicals, alkyloxyalkyl radicals, hydroxyalkyl radicals and alkylthioalkyl radicals.

It is preferred that $R^{12}$ is defined as follows: unsubstituted and mono- or polysubstituted, branched and straight-chain $(C_1-C_{18})$-alkyl radicals, $(C_3-C_{18})$-cycloalkyl radicals, $(C_2-C_{26})$-alkenyl radicals having one or more double bonds, $(C_2-C_{26})$-alkynyl radicals having one or more triple bonds, $(C_6-C_{10})$-aryl radicals, especially phenyl radicals, $(C_1-C_{18})$-alkyl-$(C_6-C_{10})$-aryl radicals, $(C_6-C_{10})$-aryl-$(C_1-C_{18})$-alkyl radicals, $(C_6-C_{10})$-aryl-$(C_2-C_{18})$-alkenyl radicals, $(C_1-C_{18})$-alkyloxy-$(C_1-C_{18})$-alkyl radicals, $(C_1-C_{18})$-hydroxyalkyl radicals and $(C_1-C_{18})$-alkylthio-$(C_1-C_{18})$-alkyl radicals, any substituents being selected from the group comprising OH, $OR^{22}$, $NH_2$, $NHR^{22}$, $NR^{22}R^{32}$, Cl, Br, I and F, where $R^{22}$ and $R^{32}$ are each independently selected from the group comprising H, unsubstituted and mono- or polysubstituted, branched and straight-chain $(C_1-C_{18})$-alkyl radicals, $(C_3-C_{18})$-cycloalkyl radicals, $(C_2-C_{26})$-alkenyl radicals having one or more double bonds, $(C_6-C_{10})$-aryl radicals, especially phenyl radicals, $(C_1-C_{18})$-alkyl-$(C_6-C_{10})$-aryl radicals, $(C_6-C_{10})$-aryl-$(C_1-C_{18})$-alkyl radicals, especially benzyl radicals, $(C_1-C_{18})$-alkyloxy-$(C_1-C_{18})$-alkyl radicals, $(C_1-C_{18})$-hydroxyalkyl radicals and $(C_1-C_{18})$-alkylthio-$(C_1-C_{18})$-alkyl radicals.

In a preferred process, the organic acid is selected from the group of p-toluenesulphonic acid, camphor-10-sulphonic acid, benzenesulphonic acid, dodecylbenzenesulphonic acid, naphthalenesulphonic acids, phenolsulphonic acids.

In a further process according to the present invention, the organic acid is a phosphonic acid of the general formula III:

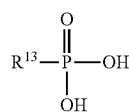

III where $R^{13}$ is an organic radical selected from the group comprising unsubstituted and mono- or polysubstituted, branched and straight-chain alkyl radicals, cycloalkyl radicals, alkenyl radicals having one or more double bonds, alkynyl radicals having one or more triple bonds, aryl radicals, alkylaryl radicals, arylalkyl radicals, arylalkenyl radicals, alkyloxyalkyl radicals, hydroxyalkyl radicals and alkylthioalkyl radicals.

In a preferred process, $R^{13}$ is defined as follows: unsubstituted and mono- or polysubstituted, branched and straight-chain $(C_1-C_{18})$-alkyl radicals, $(C_3-C_{18})$-cycloalkyl radicals, $(C_2-C_{26})$-alkenyl radicals having one or more double bonds, $(C_2-C_{26})$-alkynyl radicals having one or more triple bonds, $(C_6-C_{10})$-aryl radicals, especially phenyl radicals, $(C_1-C_{18})$-alkyl-$(C_6-C_{10})$-aryl radicals, $(C_6-C_{10})$-aryl-$(C_1-C_{18})$-alkyl radicals, $(C_6-C_{10})$-aryl-$(C_2-C_{18})$-alkenyl radicals, $(C_1-C_{18})$-alkyloxy-$(C_1-C_{18})$-alkyl radicals, $(C_1-C_{18})$-hydroxyalkyl radicals and $(C_1-C_{18})$-alkylthio-$(C_1-C_{18})$-alkyl radicals, any substituents being selected from the group comprising OH, $OR^{23}$, $NH_2$, $NHR^{23}$, $NR^{23}R^{33}$, Cl, Br, I and F, where $R^{23}$ and $R^{33}$ are each independently selected from the group comprising H, unsubstituted and mono- or polysubstituted, branched and straight-chain $(C_1-C_{18})$-alkyl radicals, $(C_3-C_{18})$-cycloalkyl radicals, $(C_2-C_{26})$-alkenyl radicals having one or more double bonds, $(C_6-C_{10})$-aryl radicals, especially phenyl radicals, $(C_1-C_{18})$-alkyl-$(C_6-C_{10})$-aryl radicals, $(C_6-C_{10})$-aryl-$(C_1-C_{18})$-alkyl radicals, especially benzyl radicals, $(C_1-C_{18})$-alkyloxy-$(C_1-C_{18})$-alkyl radicals, $(C_1-C_{18})$-hydroxyalkyl radicals and $(C_1-C_{18})$-alkylthio-$(C_1-C_{18})$-alkyl radicals.

In a preferred process, the organic acid is selected from the group of 1-aminopropylphosphonic acid, aminomethylphosphonic acid, xylenephosphonic acids, phenylphosphonic acid, 1-aminopropylphosphonic acid, toluenephosphonic acid.

In a further process, the organic acid is an alpha-hydroxycarboxylic acid of the general formula Ia

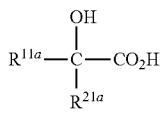

where $R^{11a}$ and $R^{21a}$ are each independently selected from the group comprising H, OH, $OR^{31a}$, $NH_2$, $NHR^{31a}$, $NR^{31a}R^{41a}$, Cl, Br, I, F, unsubstituted and mono- or polysubstituted, branched and straight-chain alkyl radicals, cycloalkyl radicals, alkenyl radicals having one or more double bonds, alkynyl radicals having one or more triple bonds, aryl radicals, alkylaryl radicals, arylalkyl radicals, arylalkenyl radicals, alkyloxyalkyl radicals, hydroxyalkyl radicals and alkylthioalkyl radicals, where $R^{31a}$ and $R^{41a}$ are each independently selected from the group comprising H, unsubstituted and mono- or polysubstituted, straight-chain and branched $(C_1-C_{18})$-alkyl radicals, $(C_3-C_{18})$-cycloalkyl radicals, $(C_2-C_{26})$-alkenyl radicals having one or more double bonds, $(C_6-C_{10})$-aryl radicals, especially phenyl radicals, $(C_1-C_{18})$-alkyl-$(C_6-C_{10})$-aryl radicals, $(C_6-C_{10})$-aryl-$(C_1-C_{18})$-alkyl radicals, especially benzyl radicals, $(C_1-C_{18})$-alkyloxy-$(C_1-C_{18})$-alkyl radicals, $(C_1-C_{18})$-hydroxyalkyl radicals and $(C_1-C_{18})$-alkylthio-$(C_1-C_{18})$-alkyl radicals.

It is further preferred that $R^{11a}$ and $R^{21a}$ are each independently selected from the group of unsubstituted and mono- or polysubstituted, branched and straight-chain $(C_1-C_{18})$-alkyl radicals, $(C_3-C_{18})$-cycloalkyl radicals, $(C_2-C_{26})$-alkenyl radicals having one or more double bonds, $(C_2-C_{26})$-alkynyl radicals having one or more triple bonds, $(C_6-C_{10})$-aryl radicals, especially phenyl radicals, $(C_1-C_{18})$-alkyl-$(C_6-C_{10})$-aryl radicals, $(C_6-C_{10})$-aryl-$(C_1-C_{18})$-alkyl radicals, $(C_6-C_{10})$-aryl-$(C_2-C_{18})$-alkenyl radicals, $(C_1-C_{18})$-alkyloxy-$(C_1-C_{18})$-alkyl radicals, $(C_1-C_{18})$-hydroxyalkyl radicals and $(C_1-C_{18})$-alkylthio-$(C_1-C_{18})$-alkyl radicals, any substituents being selected from the group comprising OH, $OR^{31a}$, $NH_2$, $NHR^{31a}$, $NR^{31a}R^{41a}$, Cl, Br, I and F, where $R^{31a}$ and $R^{41a}$ are each independently selected from the group comprising H, unsubstituted and mono- or polysubstituted, branched and straight-chain $(C_1-C_{18})$-alkyl radicals, $(C_3-C_{18})$-cycloalkyl radicals, $(C_2-C_{26})$-alkenyl radicals having one or more double bonds, $(C_6-C_{10})$-aryl radicals, especially phenyl radicals, $(C_1-C_{18})$-alkyl-$(C_6-C_{10})$-aryl radicals, $(C_6-C_{10})$-aryl-$(C_1-C_{18})$-alkyl radicals, especially benzyl radicals, $(C_1-C_{18})$-alkyloxy-$(C_1-C_{18})$-alkyl radicals, $(C_1-C_{18})$-hydroxyalkyl radicals and $(C_1-C_{18})$-alkylthio-$(C_1-C_{18})$-alkyl radicals.

In a preferred process, the organic acid is selected from the group of 2-hydroxyisobutyric acid, 2-hydroxy-4-methylthiobutyric acid, lactic acid, glycolic acid, malic acid, tartaric acid, gluconic acid, glyceric acid.

In a further preferred process, the organic acid is a beta-hydroxycarboxylic acid of the general formula Ib

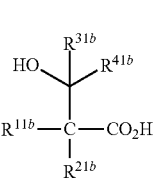

where $R^{11b}$, $R^{21b}$, $R^{31b}$ and $R^{41b}$ are each independently selected from the group comprising H, OH, $OR^{51b}$, $NH_2$, $NHR^{51b}$, $NR^{51b}R^{61b}$, Cl, Br, I, F, unsubstituted and mono- or polysubstituted, branched and straight-chain alkyl radicals, cycloalkyl radicals, alkenyl radicals having one or more double bonds, alkynyl radicals having one or more triple bonds, aryl radicals, alkylaryl radicals, arylalkyl radicals, arylalkenyl radicals, alkyloxyalkyl radicals, hydroxyalkyl radicals and alkylthioalkyl radicals, where $R^{51b}$ and $R^{61b}$ are each independently selected from the group comprising H, unsubstituted and mono- or polysubstituted, straight-chain and branched $(C_1-C_{18})$-alkyl radicals, $(C_3-C_{18})$-cycloalkyl radicals, $(C_2-C_{26})$-alkenyl radicals having one or more double bonds, $(C_6-C_{10})$-aryl radicals, especially phenyl radicals, $(C_1-C_{18})$-alkyl-$(C_6-C_{10})$-aryl radicals, $(C_6-C_{10})$-aryl-$(C_1-C_{18})$-alkyl radicals, especially benzyl radicals, $(C_1-C_{18})$-alkyloxy-$(C_1-C_{18})$-alkyl radicals, $(C_1-C_{18})$-hydroxyalkyl radicals and $(C_1-C_{18})$-alkylthio-$(C_1-C_{18})$-alkyl radicals.

It is further preferred that $R^{11b}$, $R^{21b}$, $R^{31b}$ and $R^{41b}$ are each independently selected from the group of unsubstituted and mono- or polysubstituted, branched and straight-chain $(C_1-C_{18})$-alkyl radicals, $(C_3-C_{18})$-cycloalkyl radicals, $(C_2-C_{26})$-alkenyl radicals having one or more double bonds, $(C_2-C_{26})$-alkynyl radicals having one or more triple bonds, $(C_6-C_{10})$-aryl radicals, especially phenyl radicals, $(C_1-C_{18})$-alkyl-$(C_6-C_{10})$-aryl radicals, $(C_6-C_{10})$-aryl-$(C_1-C_{18})$-alkyl radicals, $(C_6-C_{10})$-aryl-$(C_2-C_{18})$-alkenyl radicals, $(C_1-C_{18})$-alkyloxy-$(C_1-C_{18})$-alkyl radicals, $(C_1-C_{18})$-hydroxyalkyl radicals and $(C_1-C_{18})$-alkylthio-$(C_1-C_{18})$-alkyl radicals, any substituents being selected from the group comprising OH, $OR^{51b}$, $NH_2$, $NHR^{51b}$, $NR^{51b}R^{61b}$, Cl, Br, I and F, where $R^{51b}$ and $R^{61b}$ are each independently selected from the group comprising H, unsubstituted and mono- or polysubstituted, branched and straight-chain $(C_1-C_{18})$-alkyl radicals, $(C_3-C_{18})$-cycloalkyl radicals, $(C_2-C_{26})$-alkenyl radicals having one or more double bonds, $(C_6-C_{10})$-aryl radicals, especially phenyl radicals, $(C_1-C_{18})$-alkyl-$(C_6-C_{10})$-aryl radicals, $(C_6-C_{10})$-aryl-$(C_1-C_{18})$-alkyl radicals, especially benzyl radicals, $(C_1-C_{18})$-alkyloxy-$(C_1-C_{18})$-alkyl radicals, $(C_1-C_{18})$-hydroxyalkyl radicals and $(C_1-C_{18})$-alkylthio-$(C_1-C_{18})$-alkyl radicals.

In a preferred process, the organic acid is selected from the group of 3-hydroxypropionic acid, 3-hydroxybutyric acid, 3-hydroxyvaleric acid, 3-hydroxyhexanoic acid, 3-hydroxyheptanoic acid, 3-hydroxyoctanoic acid and 3-hydroxyisobutyric acid.

In a further preferred process, the stripping medium or entraining gas used is steam, air, gases, preferably natural gas, methane, oxygen, inert gas, preferably nitrogen, helium, argon, or mixtures thereof.

With regard to the introduction of the entraining gas, based on the volume $V_{aq}$ of the aqueous phase in the process, a total amount of entraining gas of preferably 10 $V_{aq}$ to 10 000 $V_{aq}$, more preferably 50 $V_{aq}$ to 5000 $V_{aq}$ and especially 100 $V_{aq}$ to 3000 $V_{aq}$ is used.

When the process according to the invention is conducted continuously with a volume flow $F_{aq}$ of the aqueous phase, a volume flow of the entraining gas of preferably 10 $F_{aq}$ to 10 000 $F_{aq}$, more preferably 50 $F_{aq}$ to 5000 $F_{aq}$ and especially 100 $F_{aq}$ to 3000 $F_{aq}$ is used.

In further preferred processes, the free acid is obtained from the extractant laden with the extracted acid by a separation process selected from distillation, rectification, crystallization, re-extraction, chromatography, adsorption or a membrane process.

One advantage of the process according to the invention is that of being less expensive, since the expensive workup and/or disposal of the amounts of salt obtained in equimolar amounts is eliminated, and another is that the back-integration of the ammonia released into a production process and the closed circuit of the extractant causes it to work in an environmentally friendly and resource-protective manner. The use of otherwise much-used assistants, for example sulphuric acid to release the free acid from the ammonium salt, is eliminated, just like additional reaction steps associated with relatively high costs.

The process works in a more energy-saving manner, since the reactive extraction can be performed at lower temperatures than the thermal salt dissociation. Employment of high pressures is unnecessary; this lowers the capital costs of an industrial plant. By virtue of the use of a stripping medium or entraining gas, the release of the acid and the extraction thereof succeed within significantly shorter reaction times and with significantly higher yields. The reactive extraction described here is thus more economically viable than the processes described in the prior art.

The novel process described here for releasing acids from the ammonium salts thereof is more economically viable and more environmentally friendly.

DESCRIPTION OF THE INVENTION

The invention described here comprises an improved process for releasing a substituted or unsubstituted organic acid, preferably a carboxylic acid (I), sulphonic acid (II) or phosphonic acid (III), more preferably an alpha-hydroxycarboxylic acid (Ia) or a beta-hydroxycarboxylic acid (Ib), from the ammonium salt (IV, V or VI) thereof by releasing and removing ammonia and simultaneously extracting the acid released from the aqueous phase with an amine extractant (Scheme 3).

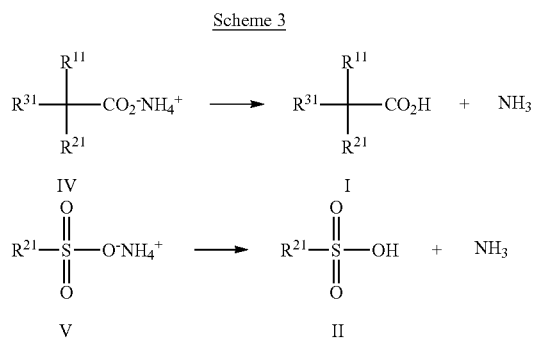

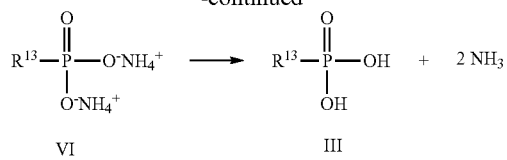

This process corresponds to a reactive extraction. The reactive extraction of an organic acid from the aqueous ammonium salt solution thereof can be improved significantly by the use of a stripping medium or entraining gas, for example nitrogen, air, steam or inert gases, for example argon. The ammonia released is removed from the aqueous solution by the continuous gas stream and can be fed back into a production process. The free acid can be obtained from the extractant by a process such as distillation, rectification, crystallization, re-extraction, chromatography, adsorption, or by a membrane process.

Extraction is understood to mean a separation process in which the enrichment or recovery of substances from mixtures is achieved with the aid of selective solvents or extractants. As in all thermal separation processes, the separation in the extraction is based on the different distribution of mixture components between two or more coexisting phases, which normally arise through the limited miscibility of the individual components with one another (miscibility gap). The mass transfer over the phase interface proceeds through diffusion until a stable end state—the thermodynamic equilibrium—has been established. After equilibrium has been attained, the phases must be separable mechanically. Since these again consist of a plurality of components, further separation processes (for example distillation, crystallization or extraction) for workup are generally connected downstream.

In the reactive extraction, at least one reaction is superimposed on the extraction. This influences the thermodynamic equilibria and thus improves the mass transfer between the phases.

It has now been found that the reactive extraction of organic acids such as carboxylic acids, sulphonic acids and phosphonic acids and especially of alpha- and beta-hydroxycarboxylic acids from the aqueous ammonium salt solutions thereof can be improved by the use of a stripping medium or entraining gas, for example nitrogen, air, steam or inert gases, for example argon. The ammonia released is removed from the aqueous solution by the continuous gas stream. This shifts the equilibrium of the reaction significantly to the right (Scheme 4, using the example of carboxylic acids).

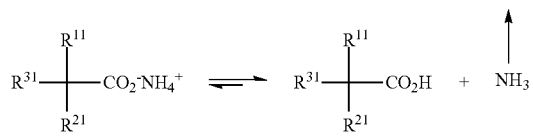

The free acid formed is extracted immediately from the aqueous solution. This does not cause any significant lowering of the pH of the aqueous solution; the release of further ammonia is not hindered.

It has been found that the temperature has a great influence on the extraction rate. The higher the temperature of the aqueous ammonium salt solution, the more rapidly the reactive extraction proceeds.

Although reactive extraction is based on the use of amines as extractants, it may be advantageous to use further coextractants in the process according to the invention, in order, for example, to influence the viscosity of the amine used. Usable coextractants are all water-immiscible or only sparingly water-miscible organic solvents such as alcohols, ethers, ketones or hydrocarbons, or mixtures thereof.

Examples are straight-chain or branched aliphatic ketones having 5 to 18 carbon atoms, cyclic, optionally heterocyclic, ketones having 6 to 18 carbon atoms, straight-chain or branched aliphatic alcohols having 4 to 18 carbon atoms, cyclic, optionally heterocyclic, alcohols having 5 to 18 carbon atoms, straight-chain or branched aliphatic alkanes having 5 to 16 carbon atoms, cycloalkanes having 5 to 14 carbon atoms, straight-chain or branched ethers having 4 to 14 carbon atoms, aromatics substituted by halogen atoms or hydroxyl groups, straight-chain or branched alkanes which are substituted by halogen atoms and have 1 to 18 carbon atoms, cycloalkanes which are substituted by halogen atoms and have 5 to 14 carbon atoms.

Coextractants added with preference are selected from the group of isobutyl methyl ketone, isopropyl methyl ketone, ethyl methyl ketone, butyl methyl ketone, ethyl propyl ketone, methyl pentyl ketone, ethyl butyl ketone, dipropyl ketone, hexyl methyl ketone, ethyl pentyl ketone, heptyl methyl ketone, dibutyl ketone, 2-undecanone, 2-dodecanone, cyclohexanone, cyclopentanone, 1-butanol, 2-butanol, 1-pentanol, 1-hexanol, 2-hexanol, 3-hexanol, 1-heptanol, 2-heptanol, 3-heptanol, 1-octanol, 2-octanol, 3-octanol, 4-octanol, 1-nonanol, 2-nonanol, 3-nonanol, 5-nonanol, 1-decanol, 2-decanol, 1-undecanol, 2-undecanol, 1-dodecanol, 2-dodecanol, cyclopentanol, cyclohexanol, kerosene, petroleum benzine, pentane, hexane, heptane, octane, nonane, decane, undecane, dodecane, cyclopentane, cyclohexane, cycloheptane, methyl tert-butyl ether, petroleum ether, dibutyl ether, diisopropyl ether, dipropyl ether, diethyl ether, ethyl tert-butyl ether, dipentyl ether, benzene, toluene, o-xylene, m-xylene, p-xylene, chlorobenzene, dichloromethane, chloroform and tetrachloromethane.

Preference is given to adding, to the amine used as the extractant, coextractants in amounts of less than 80% by weight, preferably of less than 60% by weight and more preferably of less than 50% by weight, based on the total amount of the extractant.

In the case that the boiling point of the organic extractant is less than the boiling point of the acid to be extracted, the process according to the invention can be performed in a specially developed perforator (FIG. 1).

The specific perforator is equipped with a distributor inserted into the extraction vessel. The distributor is rotated by means of a magnetic coupling. The extractant supplied to this distributor from the condenser above through a tube is thrown by centrifugal force out of small holes of a distributor ring as fine droplets into the liquid to be extracted. This achieves fine distribution and intimate mixing of the extractant with the material for extraction. This ensures optimal mass transfer. As a result of the co-rotation of the liquid to be extracted, the finely distributed extractant laden with the substance extracted reaches the deposition zone of the perforator only after a prolonged residence time in the material for extraction and runs back into the distillation flask, from which the solvent is recycled into the extraction circuit by re-evaporation.

In the case that the boiling point of the organic extractant is greater than the boiling point of the acid to be extracted, the process according to the invention can be performed in an apparatus as shown in (FIG. 2).

A two-neck flask is initially charged with an aqueous solution of the salt together with the high boiling extractant. The temperature within the column can be adjusted as desired using an oil bath and is always set to a temperature below the boiling temperature of the mixture. The biphasic system is mixed by means of a magnetic stirrer in order to achieve a maximum interface between the aqueous phase and the extraction phase. The free acid accumulates in the extraction phase. A frit is used to introduce nitrogen into the stirred phases, which strips the ammonia out of the system. The salt is thus separated into the free acid and the corresponding base. Atop the flask is a column with random packing, atop which is in turn a condenser. As a result of the partial pressure of the water, the latter is stripped continuously out of the two-neck flask in small amounts and condensed in the condenser. Owing to the dissolution capacity of ammonia in water, the condensed water is separated from the ammonia in the column before it drips back into the two-neck flask. For a mass balance of the ammonia, a wash bottle is connected downstream of the condenser, in which the ammonia which has been stripped out is dissolved.

Separation Processes

In order to separate the free acid from the extractant on completion of extraction, various processes are employable:

For example, the extractant laden with the free acid can be cooled in a phase separator. The free organic acid separates out as a more highly concentrated aqueous phase with the water dissolved in the extractant and can be removed thus. After distillative removal of the water, the free acid is present in pure form. The extractant can be fed directly back into the extraction circuit.

Distillative removal of the extractant is also possible. The extractant laden with the free acid is heated to boiling and distilled off at standard pressure or reduced pressure in a distillation apparatus of customary design. This distillate, which contains water in the case of an azeotrope-forming solvent or else is anhydrous, can be fed directly back into the extraction circuit. The free acid remains in the distillation bottoms.

A further means of removing the free acid from the laden extractant is re-extraction with water. To this end, the extractant laden with the free acid is re-extracted from the organic solvent with water in a countercurrent extraction in an extraction apparatus (e.g. FIG. 2). According to the degree of extraction, a one-stage or multistage extraction is necessary. The organic extractant which is now unladen again can be fed directly back into the extraction circuit. The aqueous solution of the free acid can be concentrated to the desired concentration by distillative removal of the water.

According to the type of acid used, the removal from the organic extractant can also be effected by crystallization, adsorption, membrane processes, chromatography, rectification, or the like.

Means of Industrial Implementation

Process description for isolation of the free acid from the salts thereof.

FIG. 3 describes one configuration of the process according to the invention, in which the free acid is extracted from the salts thereof with suitable amines as extractants:

In a column, the aqueous phase laden with the salts of the acid is contacted with the organic extractant. The column here may be configured either as a bubble column or as a filled or stirred column. The salt is dissociated within the column. The acid is extracted into the phase of the organic extractant and the depleted aqueous phase leaves the column at the bottom. The ammonia which forms as the corresponding base is stripped out of the column by a carrier gas which is introduced at the bottom of the column. For regeneration, this ammonia-laden carrier gas stream can be passed over a sorbent on which the base is sorbed. The depleted carrier gas stream can thus be fed back to the process. A desorption regenerates both the base and the sorbent, and they are used alternately for sorption and desorption. Connected to the desorption is a scrubber in which the ammonia is recovered as an aqueous solution and can be provided again to the fermentation as the base. It is thus possible to achieve a closed circuit for the ammonia.

The laden organic extractant from the column is regenerated in a rectification after a phase separation. The free acid is thus separated thermally from the organic extractant and obtained as the product. The organic extractant can, after separation of the organic extractant from the free acid, be sent back to the process.

Analogously, the $NH_3$ removed from the aqueous solution can be sent back to the process.

In addition, the processes of the present invention can be performed in batchwise mode, known to those skilled in the art, or in continuous mode.

EXAMPLES

Example 1

Figure 1:
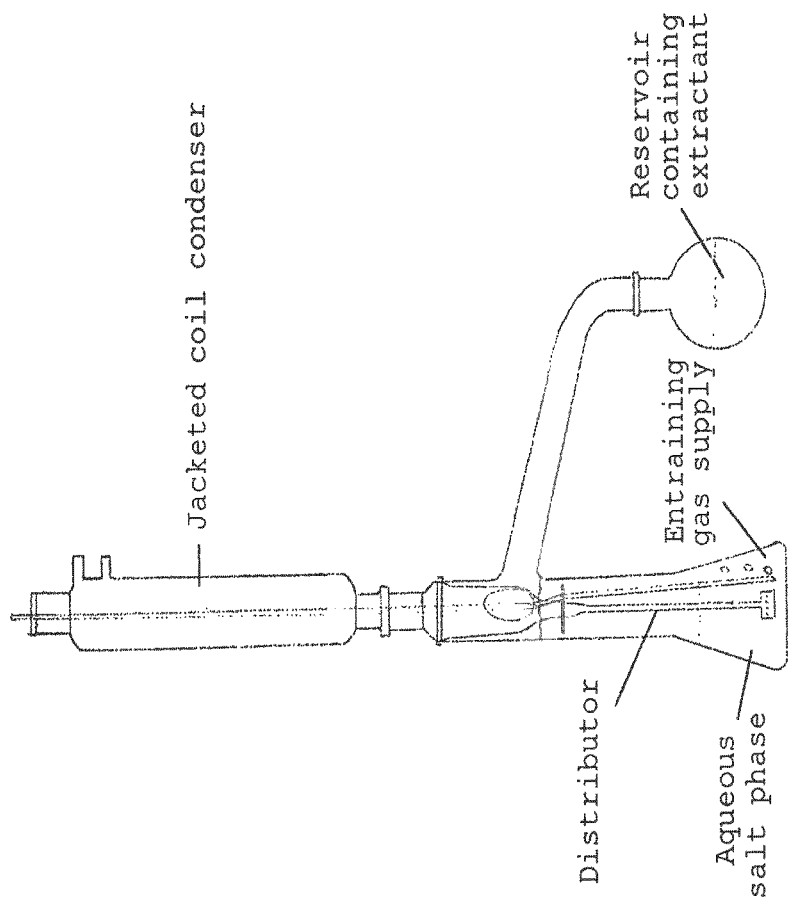
FIG. 1 shows the schematic setup of an example of a perforator for use in the process according to the invention for reactive extraction.
Figure 2:
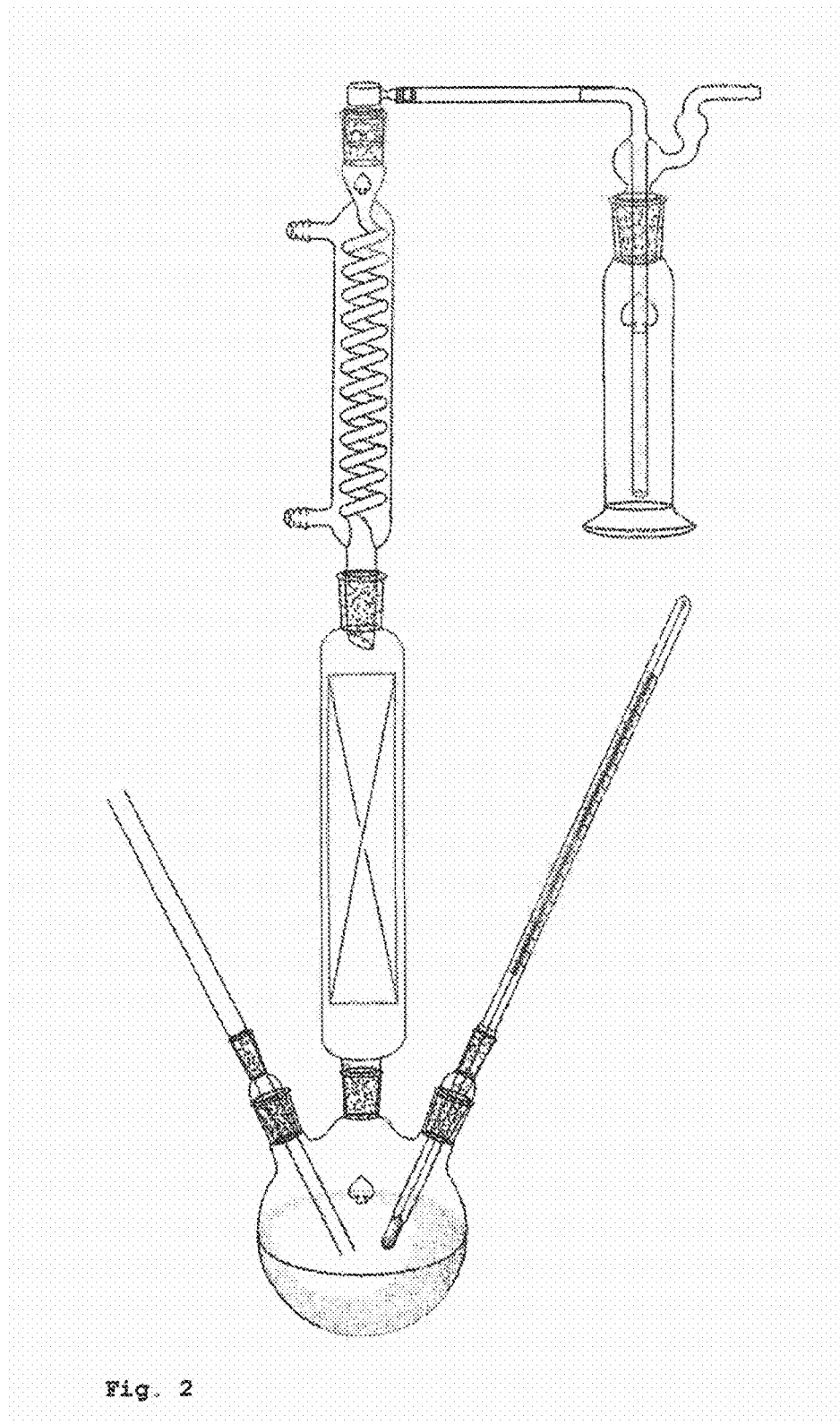
FIG. 2 shows the schematic setup of the extraction apparatus used.
Figure 3:
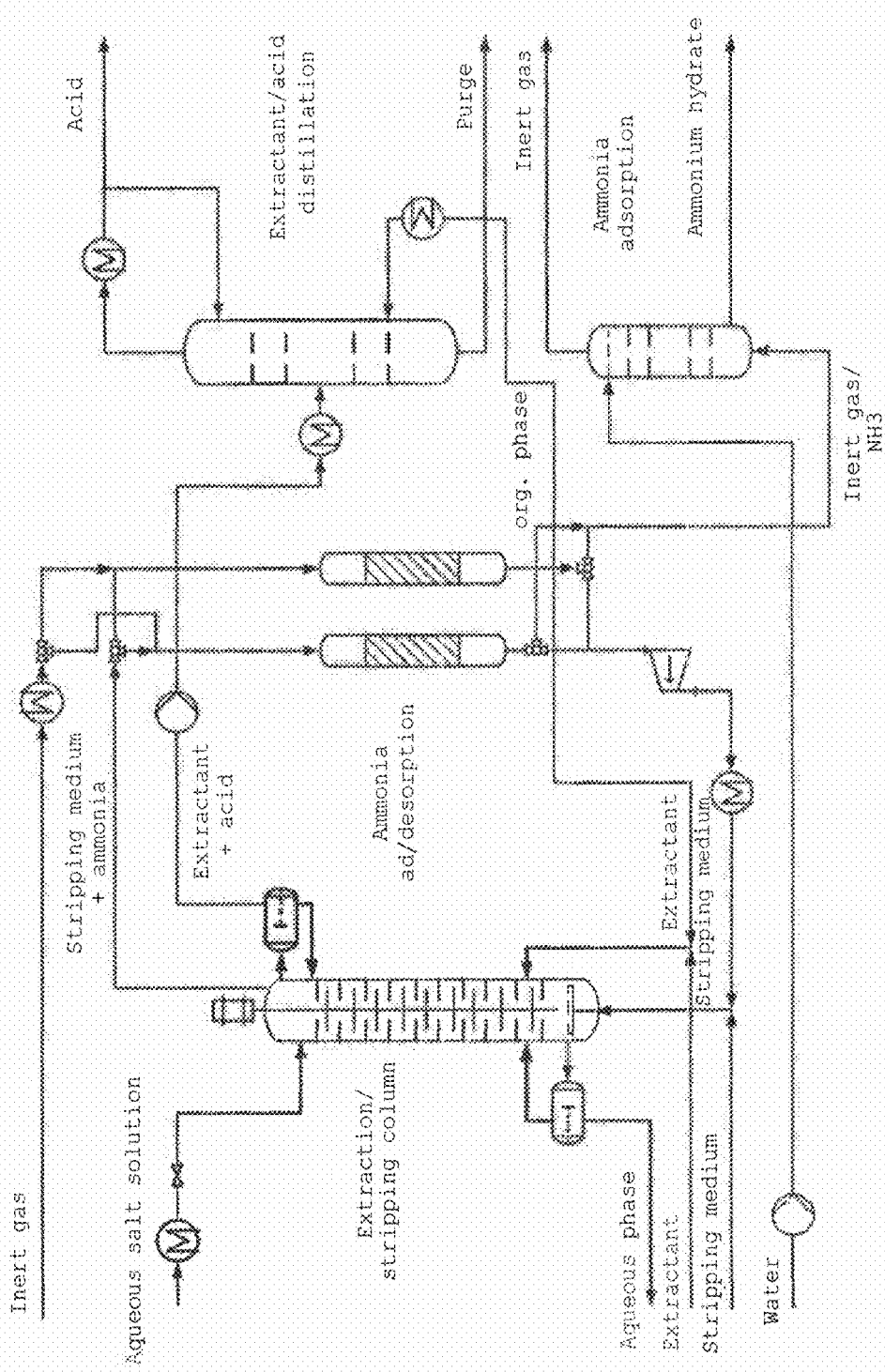
FIG. 3 shows the schematic setup of an industrial inventive reactive extraction.

Reactive Extraction of 2-Hydroxyisobutyric Acid from a 10% by Weight Ammonium 2-Hydroxyisobutyrate Solution with Diisotridecylamine The example described hereinafter was performed in the apparatus shown in FIG. 2.

A three-neck flask was initially charged with 85.07 g of a 10% by weight ammonium 2-hydroxyisobutyrate solution and 85.04 g of diisotridecylamine. The two phases were mixed vigorously with a magnetic stirrer. The 3-neck flask was heated to 95° C. at ambient pressure in an oil bath. A glass frit for nitrogen stripping was inserted into one of the lateral orifices of the flask, and a gas flow of 20 l/h was established. A thermometer to measure the internal temperature was inserted into the second lateral orifice. A column with random packing (approx. 0.7 m) was inserted into the remaining orifice of the 3-neck flask. At the upper end of the column was mounted a jacketed coil condenser. Connected thereto was a wash bottle filled with 107.66 g of dilute sulphuric acid (1 mol/l), in which the ammonia which had been stripped out was absorbed for mass balancing. After 20 h, the experiment was interrupted for mass balancing, and stopped after a further 20 h. Within this time, the ammonium salt was dissociated into the free acid and ammonia. The free acid was extracted into the organic phase, and the ammonia was stripped out of the system by the nitrogen. After this total of 40 hours, a conversion of the ammonium 2-hydroxyisobutyrate of approx. 80% was achieved. The yield of alkylammonium 2-hydroxyisobutyrate was likewise approx. 80%.

Example 2

Reactive Extraction of 2-Hydroxyisobutyric Acid from a 10% by Weight Ammonium 2-Hydroxyisobutyrate Solution with Trihexylamine The example described below was performed in the apparatus shown in FIG. 2.

A three-neck flask was initially charged with 99.53 g of a 10% by weight ammonium 2-hydroxyisobutyrate solution and 55.07 g of trihexylamine. The two phases were mixed vigorously with a magnetic stirrer. The 3-neck flask was heated to 95° C. at ambient pressure in an oil bath. A glass frit for nitrogen stripping with a gas flow of approx. 20 l/h and a thermometer to measure the internal temperature were inserted into the lateral orifices of the flask. A column with random packing (approx. 0.7 m) was inserted into the remaining orifice of the 3-neck flask. At the upper end of the column was mounted a jacketed coil condenser. Connected thereto was a wash bottle filled with 99.79 g of dilute sulphuric acid (1 mol/l), in which the ammonia which had been stripped out was absorbed for mass balancing. After 20 h in each case, the experiment was interrupted for mass balancing, and stopped after 60 h. Within this time, the ammonium salt was dissociated into the free acid and ammonia. A conversion of approx. 32% was achieved, and the yield of alkylammonium 2-hydroxyisobutyrate was approx. 25%.

Example 3

Reactive Extraction of 2-Hydroxyisobutyric Acid from a 10% by Weight Ammonium 2-Hydroxyisobutyrate Solution with Trioctylamine (TOA)

The example described below was carried out in the apparatus described in FIG. 2.

A three-neck flask was initially charged with 200.53 g of a 10% by weight ammonium 2-hydroxyisobutyrate solution and 200.12 g of TOA. The two phases were mixed vigorously with a magnetic stirrer. The 3-neck flask was heated to 95° C. at ambient pressure in an oil bath. A glass frit for nitrogen stripping with a gas flow of 20 l/h and a thermometer to measure the internal temperature were inserted into the lateral orifices of the flask. A column with random packing (approx. 0.7 m) was inserted into the remaining orifice of the 3-neck flask. At the upper end of the column was mounted a jacketed coil condenser. Connected to this was a wash bottle filled with 60.04 g of dilute sulphuric acid (1 mol/l), in which the ammonia which had been stripped out was absorbed for mass balancing. The experiment time was approx. 42 h. Within this time, the ammonium salt was dissociated into the free acid and ammonia. A conversion of approx. 33% was achieved, and the yield of alkylammonium 2-hydroxyisobutyrate was approx. 26%.

Example 4

Thermal Dissociation of Tertiary Amines and 2-Hydroxyisobutyric Acid

In a three-neck flask, 106 g of trioctylamine (TOA) were mixed with 20 g of 2-hydroxyisobutyric acid (2-HIBA) and separated thermally in a batch distillation. The bottoms were heated by a heating mantle and the bottom temperature was measured continuously. To reduce the partial pressure, a nitrogen flow of approx. 10 l/h was passed into the bottom flask of the apparatus. A trace-heated column filled with random packings was secured to the flask. Connected thereto was a Liebig condenser which condensed the distillate which was in turn collected in a round-bottom flask. A vacuum pump was used to establish a system pressure of 50 mbar. The distillation was conducted without reflux of the distillate. After approx. 100 min, a distillate temperature of approx. 140° C. and a bottom temperature of approx. 195° C. were established. After a further 40 min, the temperature in the distillate fell. After a total of 150 min, the bottoms reached a temperature of approx. 270° C. and the experiment was stopped. 104.3 g of TOA in the bottoms and 15.1 g of 2-hydroxyisobutyric acid in the distillate were found by weighing. An analysis of the bottoms showed a full conversion of 2-hydroxyisobutyric acid. TOA was detected in the distillate only in traces. The yield of free acid was approx. 60%.

Example 5

Thermal Dissociation of Secondary Amines (Diisotridecylamine) and 2-Hydroxyisobutyric Acid In a three-neck flask, 81 g of diisotridecylamine (DITD) were mixed with 20 g of 2-hydroxyisobutyric acid (2-HIBA), and separated thermally in a batch distillation. The bottoms were heated by a heating mantle and the bottom temperature was measured continuously. To reduce the partial pressure, a nitrogen flow of approx. 10 l/h was passed into the bottom flask of the apparatus. A trace-heated column filled with random packings was secured to the flask. Connected thereto was a Liebig condenser which condensed the distillate which was in turn collected in a round-bottom flask. A vacuum pump was used to establish a system pressure of 50 mbar. The distillation was conducted without reflux of the distillate. After approx. 130 min, a distillate temperature of approx. 120° C. and a bottom temperature of approx. 230° C. were established. After a further 45 min, the temperature in the distillate fell. After a total of 190 min, the bottoms reached a temperature of approx. 270° C. and the experiment was stopped. 71.7 g of DITD in the bottoms and 18.08 g of 2-HIBA in the distillate were found by weighing. An analysis of the bottoms showed a full conversion of 2-HIBA and the formation of small amounts of secondary amides (2 mol %) and amounts of primary amides (5 mol %). DITD could be detected in the distillate only in traces. The yield of free acid was approx. 72%.

Example 6

Reactive Extraction of 3-Hydroxyisobutyric Acid from a 10% by Weight Ammonium 3-Hydroxyisobutyrate Solution with Ditridecylamine The example described hereinafter was conducted in the apparatus shown in FIG. 2.

A three-neck flask was initially charged with 103.0 g of a 10% by weight ammonium 3-hydroxyisobutyrate solution and 76.4 g of ditridecylamine. Both phases were mixed vigorously with a magnetic stirrer. The 3-neck flask was heated in an oil bath to 95° C. at ambient pressure. In one of the lateral orifices of the flask, a glass frit was inserted for nitrogen stripping, and a gas flow of 20 l/h was established. A thermometer for measuring the internal temperature was inserted into the second lateral orifice. A column with random packing (approx. 0.7 m) was inserted into the remaining orifice of the 3-neck flask. At the upper end of the column, a jacketed coil condenser was mounted. Connected thereto was a wash bottle filled with 202.2 g of dilute sulphuric acid (1 mol/l), in which the ammonia which had been stripped out was absorbed for mass balancing. After 69 h, the experiment was ended for mass balancing. Within this time, the ammonium salt was split into the free acid and ammonia. The free acid was extracted into the organic phase, and the ammonia was stripped out of the system by the nitrogen. A conversion of the ammonium 3-hydroxyisobutyrate of approx. 54% was attained. The yield of alkylammonium 3-hydroxyisobutyrate was approx. 42%.

Example 7

Reactive Extraction of Lactic Acid from a 10% by Weight Ammonium Lactate Solution with Ditridecylamine The example described hereinafter was conducted in the apparatus shown in FIG. 2.

A three-neck flask was initially charged with 99.0 g of a 10% by weight ammonium lactate solution and 75.1 g of ditridecylamine. Both phases were mixed vigorously with a magnetic stirrer. The 3-neck flask was heated in an oil bath to 95° C. at ambient pressure. In one of the lateral orifices of the flask, a glass frit was inserted for nitrogen stripping, and a gas flow of 20 l/h was established. A thermometer for measuring the internal temperature was inserted into the second lateral orifice. A column with random packing (approx. 0.7 m) was inserted into the remaining orifice of the 3-neck flask. At the upper end of the column, a jacketed coil condenser was mounted. Connected thereto was a wash bottle filled with 186.4 g of dilute sulphuric acid (1 mol/l), in which the ammonia which had been stripped out was absorbed for mass balancing. After 60 h, the experiment was ended for mass balancing. Within this time, the ammonium salt was split into the free acid and ammonia. The free acid was extracted into the organic phase, and the ammonia was stripped out of the system by the nitrogen. A conversion of the ammonium lactate of approx. 59% was attained. The yield of alkylammonium lactate was likewise approx. 59%.

Example 8

Reactive Extraction of Succinic Acid from a 10% by Weight Ammonium Succinate Solution with Ditridecylamine The example described hereinafter was conducted in the apparatus shown in FIG. 2.

A three-neck flask was initially charged with 102.9 g of a 10% by weight ammonium succinate solution and 75.0 g of ditridecylamine. Both phases were mixed vigorously with a magnetic stirrer. The 3-neck flask was heated in an oil bath to 95° C. at ambient pressure. In one of the lateral orifices of the flask, a glass frit was inserted for nitrogen stripping, and a gas flow of 20 l/h was established. A thermometer for measuring the internal temperature was inserted into the second lateral orifice. A column with random packing (approx. 0.7 m) was inserted into the remaining orifice of the 3-neck flask. At the upper end of the column, a jacketed coil condenser was mounted. Connected thereto was a wash bottle filled with 212.2 g of dilute sulphuric acid (1 mol/l), in which the ammonia which had been stripped out was absorbed for mass balancing. After 65 h, the experiment was ended for mass balancing. Within this time, the ammonium salt was split into the free acid and ammonia. The free acid was extracted into the organic phase, and the ammonia was stripped out of the system by the nitrogen. A conversion of the ammonium succinate of approx. 48% was attained. The yield of alkylammonium succinate was approx. 43%.

The invention claimed is:

1. A process for converting at least one ammonium salt 2-hydroxyisobutyric acid to a free organic acid, the method comprising:
   (A) contacting an aqueous solution of the ammonium salt with at least one organic extractant comprising a dialkyamine; and
   (B) dissociating the salt at a temperature and pressure at which the aqueous solution and the extractant are in a liquid state;
   (C) introducing a stripping medium or entraining gas in order to remove $NH_3$ from the aqueous solution; and
   (D) transferring at least a portion of the free organic acid formed to the organic extractant.

2. The process of claim 1, wherein the dissociating is effected at a pressure in a range of 0.01 bar to 10 bar.

3. The process of claim 1, wherein the dissociating is performed at a temperature in a range of 20° C. to 300° C.

4. The process of claim 1, wherein a starting concentration of the ammonium salt of the 2-hydroxyyisobutyric acid in the aqueous solution is in a range of up to 60% by weight.

5. The process of claim 1, wherein the extractant is a sparingly water-miscible or completely water-immiscible solvent.

6. The process of claim 1, wherein a weight ratio of aqueous solution to organic extractant is from 1:100 to 100:1.

7. The process of claim 1, wherein, after the dissociating has ended, the organic acid formed is obtained from the organic extractant.

8. The process of claim 1, wherein the stripping medium or entraining gas comprises at least one selected from the group consisting of steam, air, and a gas.

9. The process of claim 1, wherein the entraining gas is present, and based on a volume $V_{aq}$ of the aqueous phase, a total amount of the entraining gas is $10V_{aq}$ to $10\,000V_{aq}$.

10. The process of claim 1, wherein the free acid is obtained from the extractant laden with the extracted acid by at least one separating process selected from the group consisting of distillation, rectification, crystallization, re-extraction, chromatography, adsorption, and a membrane process.

11. The process claim 10, wherein the separating of the organic extractant from the free acid is followed by feeding of the organic extractant separated back to the process.

12. The process of claim 1, wherein the $NH_3$ removed from the aqueous solution is fed back to the process.

* * * * *